(12) United States Patent
Moszner et al.

(10) Patent No.: US 12,083,194 B2
(45) Date of Patent: *Sep. 10, 2024

(54) DENTAL MATERIALS BASED ON POLYMERIZABLE THIOUREA DERIVATIVES

(71) Applicant: Ivoclar Vivadent AG, Schaan (LI)

(72) Inventors: Norbert Moszner, Triesen (LI); Yohann Catel, Sevelen (CH); Iris Lamparth, Grabs (CH); Jörg Angermann, Sargans (CH)

(73) Assignee: Ivoclar Vivadent AG, Schaan (LI)

( * ) Notice: Subject to any disclaimer, the term of this patent is extended or adjusted under 35 U.S.C. 154(b) by 264 days.

This patent is subject to a terminal disclaimer.

(21) Appl. No.: 17/590,421

(22) Filed: Feb. 1, 2022

(65) Prior Publication Data

US 2022/0257474 A1 Aug. 18, 2022

(30) Foreign Application Priority Data

Feb. 5, 2021 (EP) ..................................... 21155529

(51) Int. Cl.
*A61K 6/61* (2020.01)
*A61K 6/887* (2020.01)

(52) U.S. Cl.
CPC ................ *A61K 6/61* (2020.01); *A61K 6/887* (2020.01)

(58) Field of Classification Search
CPC ...................................................... A61K 6/61
See application file for complete search history.

(56) References Cited

U.S. PATENT DOCUMENTS

| | | |
|---|---|---|
| 3,991,008 A | 11/1976 | Temin et al. |
| 7,275,932 B2 | 10/2007 | Jin et al. |
| 7,498,367 B2 | 3/2009 | Qian |
| 7,541,393 B2 | 6/2009 | Mitra et al. |
| 8,247,470 B2 | 8/2012 | Yarimizu et al. |
| 2007/0040151 A1 | 2/2007 | Utterodt et al. |
| 2007/0100019 A1 | 5/2007 | Sun |
| 2010/0311864 A1 | 12/2010 | Arita et al. |
| 2020/0253837 A1 | 8/2020 | Moszner et al. |

*Primary Examiner* — Benjamin J Packard
(74) *Attorney, Agent, or Firm* — Ann M. Knab; Thad McMurray

(57) ABSTRACT

Radically polymerizable dental material, which includes a combination of a hydroperoxide and a thiourea derivative according to the following Formula (I) as initiator system for the radical polymerization:

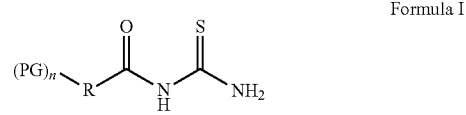

Formula I in which R is absent or is an (n+1)-valent, aromatic, aliphatic, linear or branched $C_1$-$C_{50}$ hydrocarbon radical, which can be interrupted by one or more ether, thioether, ester, amide or urethane groups; PG is a radically polymerizable (meth)acrylate, (meth)acrylamide or vinyl group; and n is 1, 2 or 3.

20 Claims, No Drawings

DENTAL MATERIALS BASED ON POLYMERIZABLE THIOUREA DERIVATIVES

CROSS-REFERENCE TO RELATED APPLICATIONS

This application claims priority to European patent application No. 21155529.7 filed on Feb. 5, 2021, the disclosure of which is incorporated herein by reference in its entirety.

TECHNICAL FIELD

The present invention relates to radically polymerizable compositions with a hydroperoxide-thiourea redox initiator system which contains radically polymerizable thiourea derivatives. The compositions are particularly suitable as dental materials, for example as prosthesis materials, cements, adhesives and composites for direct fillings.

BACKGROUND

The main areas of use of polymers in the dental field are removable prosthetics (e.g. teeth and prosthesis base materials) and fixed prosthetics (e.g. veneering materials, crowns or cements), filling materials (e.g. direct or indirect filling composites, fixing cements or adhesives) or auxiliary materials (e.g. impression materials). The polymers are usually obtained by radical polymerization of compositions which contain a polymerizable organic matrix, usually a mixture of monomers, initiator components and stabilizers.

Methyl methacrylate (MMA) (prosthesis materials), mixtures of functionalized monomers, such as e.g. 2-hydroxyethyl methacrylate (HEMA), or acid-group-containing adhesive monomers, such as e.g. 10-methacryloyloxydecyl dihydrogen phosphate (MDP), with dimethacrylates (adhesives) or mixtures which contain exclusively dimethacrylates (composite cements and filling composites) are usually used as monomers. Dimethacrylates often used are 2,2-bis[4-(2-hydroxy-3-methacryloyloxypropyl)phenyl]propane (bis-GMA) and 1,6-bis-[2-methacryloyloxyethoxycarbonylamino]-2,2,4-trimethylhexane (UDMA), which have a high viscosity and result in polymerizates with very good mechanical properties. Above all triethylene glycol dimethacrylate (TEGDMA), 1,10-decanediol dimethacrylate (D3MA) or bis(3-methacryloyloxymethyl)tricyclo-[5.2.1.0 2.6]decane (DCP) are used as reactive diluents.

Methacrylate-based dental materials are cured by radical polymerization, wherein photoinitiators (light curing, direct filling composites and adhesives), thermal initiators (indirect composites or prosthesis materials) or redox initiator systems (composite cements) are used depending on the area of use. The combination of photoinitiators with redox initiators, e.g. in the case of filling materials for deep cavities, is also usual.

Redox systems are used especially when there is the risk of incomplete curing, e.g. because of a low monomer reactivity in the case of prosthesis materials or because of insufficient irradiation in the case of fixing cements.

In order to guarantee a sufficient storage stability of the materials, materials based on redox initiators are usually used as so-called two-component systems (2C systems), wherein the oxidant (peroxide or hydroperoxide) and the reducing agent (amines, sulfinic acids, barbiturates, thiourea etc.) are incorporated into two separate components. These components are mixed with each other shortly before use. The two components must be matched such that their homogeneous blending and use is easily possible and that a processing time sufficient for dental purposes is achieved. By the processing time is meant the period of time between the blending of the two components and the start of curing of the mixed material. On the other hand, the curing time, i.e. the period until complete hardening of the materials, must not be too long.

For a long time, redox initiator systems which are based on mixtures of dibenzoyl peroxide (DBPO) with tertiary aromatic amines, such as e.g. N,N-diethanol-p-toluidine (DEPT), N,N-dimethyl-sym.-xylidine (DMSX) or N,N-diethyl-3,5-di-tert.-butylaniline (DABA), have primarily been used for dental composite cements. With DBPO/amine-based redox initiator systems the processing and curing time can be set relatively well in combination with phenolic inhibitors. A disadvantage of such DBPO/amine systems is the discolorations which are caused by a slow oxidation of the amines. Moreover, the radical formation in the case of DBPO/amine-based redox initiator systems is impaired by acids and thus also by acidic monomers, which are normally used to prepare enamel-dentine adhesives. The amine component is protonated by an acid-base reaction and thereby deactivated.

The above disadvantages can be partially overcome with hydroperoxide redox initiator systems, because no tertiary amines are needed as reducing agent. Moreover, hydroperoxides are more thermally stable than peroxides. Cumene hydroperoxide has for example a 10-hour half-life temperature $T_{1/2}$ of 158° C.; the 10-hour half-life temperature $T_{1/2}$ of DBPO is only 73° C.

DE 26 35 595 C2 and corresponding U.S. Pat. No. 3,991,008, which US patent is hereby incorporated by reference, disclose polymerizable dental filling compounds which contain a substituted thiourea reducing agent in combination with a hydroperoxide oxidant as initiator system. The materials are said to have an improved colour stability and storage life and a good cure rate.

EP 1 693 046 B1 and corresponding U.S. Pat. No. 7,498,367, which US patent is hereby incorporated by reference, disclose dental cements and core build-up materials which contain a (2-pyridyl)-2-thiourea derivative in combination with a hydroperoxide, in which the hydroperoxide group is bonded to a tertiary carbon atom.

WO 2007/016508 A1 and corresponding US 20070100019, which US published application is hereby incorporated by reference, disclose polymerizable dental compositions which contain a thiourea derivative in combination with a hydroperoxide as initiator system. The compositions do not contain monomers with acid groups.

According to EP 1 754 465 B1 and corresponding US 20070040151, which US published application is hereby incorporated by reference, the reactivity of the cumene hydroperoxide/acetyl thiourea system can be increased by the addition of soluble copper compounds.

U.S. Pat. No. 7,275,932 B2, which US patent is hereby incorporated by reference, proposes the use of hydroperoxides and thiourea derivatives in combination with acidic compounds as accelerator. Preferred acidic compounds are acrylates and methacrylates with acid groups such as e.g. methacrylic acid.

EP 2 233 544 A1 and corresponding U.S. Pat. No. 8,247,470 B2 and EP 2 258 336 A1 and corresponding US 20100311864 A1, which US patent and published application are hereby incorporated by reference, disclose dental materials which contain a hydroperoxide and a thiourea derivative in combination with a vanadium compound as accelerator.

WO 03/057792 A2 and corresponding U.S. Pat. No. 7,541,393 B2, which US patent is hereby incorporated by reference, disclose discloses dental materials which contain polymerizable thiourea derivatives such as allyl thiourea, 1-allyl-3-(2-hydroxyethyl)-2-thiourea or methacrylic acid 4-oxo-9-thioxo-5-oxa-3,8,10-triazatridec-12-en-1-yl ester as reducing agent. These are to have a lower risk of potential toxic or narcotic side effects.

Initiator systems based on hydroperoxides and thiourea derivatives have gained considerable importance in the avoidance of the disadvantages associated with peroxide/amine systems. A disadvantage is that many thiourea derivatives have an intense bitter taste (D. Mela, Chem. Senses 14 (1989) 131-135; Lange et al., Chem. Amer. Chem. Soc. 51 (1929) 1911-1914; Qin et al., Talanta 199 (2019) 131-139) which is still noticeable even after hardening, which is perceived as unpleasant by many patients.

SUMMARY

The object of the invention is to provide dental materials which do not have the disadvantages of the state of the art. The materials are not to taste bitter, are to have a good biocompatibility and good curing characteristics and to have good mechanical properties.

DETAILED DESCRIPTION

This object is achieved by radically polymerizable dental materials which contain a combination of a hydroperoxide and a thiourea derivative according to the following Formula (I) as initiator system for the radical polymerization:

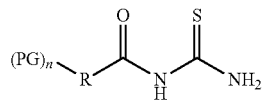

Formula I in which the variables have the following meanings:

R is absent or an (n+1)-valent, aromatic, aliphatic, linear or branched $C_1$-$C_{50}$ hydrocarbon radical, which can be interrupted by one or more, preferably 1 to 8, particularly preferably 1 to 6, ether, thioether, ester, amide or urethane groups, PG a radically polymerizable (meth)acrylate, (meth)acrylamide or vinyl group, n is 1, 2 or 3.

The variables preferably have the following meanings:

R an (n+1)-valent, aromatic, aliphatic, linear or branched $C_1$-$C_{30}$ hydrocarbon radical, which can be interrupted by one or more, preferably 1 to 6, particularly preferably 1 to 3, ether, ester or urethane groups, PG a radically polymerizable methacrylate or vinyl group and n is 1 or 2.

The variables particularly preferably have the following meanings:

R an (n+1)-valent, aliphatic, linear or branched $C_1$-$C_{20}$ hydrocarbon radical, which can be interrupted by 1 to 6 ether groups or one (1) ester or urethane group, PG a radically polymerizable methacrylate or vinyl group and n is 1 or

R a phenylene radical, preferably a p-phenylene radical, or a radical with the formula -Ph-$CH_2$—, PG a vinyl group and n is 1, wherein, when R is -Ph-$CH_2$—, the vinyl group is bonded to the phenyl radical (Ph): $H_2C$=$CH$-Ph-$CH_2$—.

All formulae shown herein extend only to those compounds which are compatible with the theory of chemical valence. The indication that a radical is interrupted e.g. by one or more ether groups is to be understood to mean that these groups are inserted in each case into the carbon chain of the radical. These groups are thus bordered on both sides by C atoms and cannot be terminal. $C_1$ radicals cannot be interrupted. Corresponding to the usual nomenclature, by aromatic hydrocarbon radicals is also meant those radicals which contain aromatic and non-aromatic groups. A preferred aromatic radical is, for example, -Ph-$CH_2$—.

The preferred, particularly preferred and quite particularly preferred definitions given for the individual variables can be selected in each case independently of each other. Compounds in which all the variables have the preferred, particularly preferred and quite particularly preferred definitions are naturally particularly suitable according to the invention.

Thiourea derivatives of Formula I are not known, but can be prepared using known synthesis methods. For example, polymerizable benzoyl and acetyl thiourea derivatives can be prepared by reaction of the corresponding polymerizable acid chlorides with thiourea at elevated temperatures:

1st Stage:

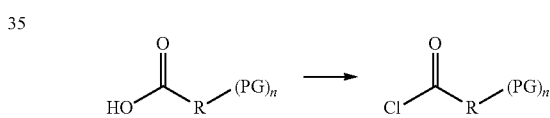

Specific Examples:

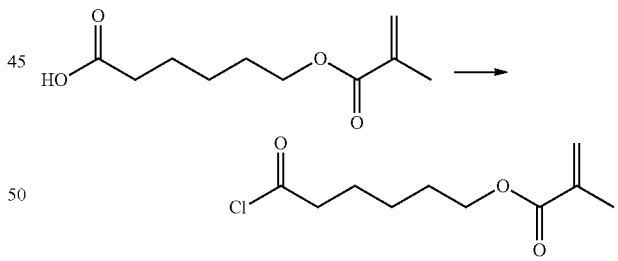

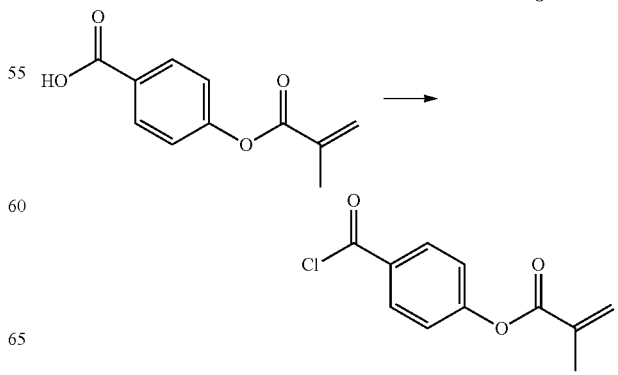

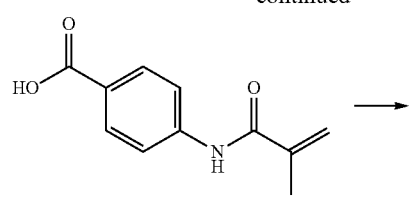
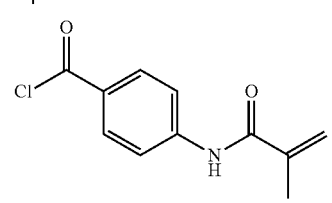
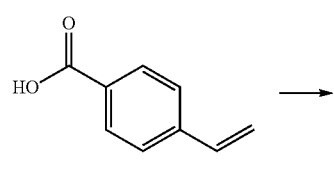
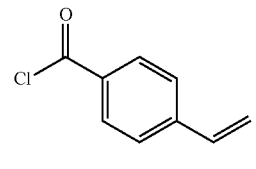
2nd Stage:
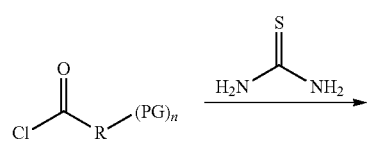
Specific Examples:
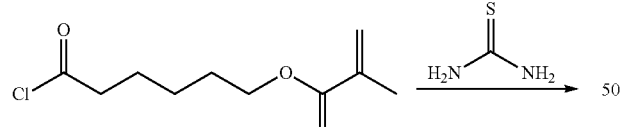
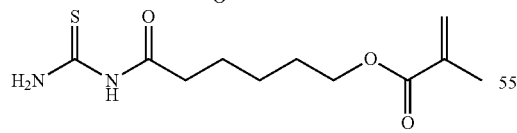
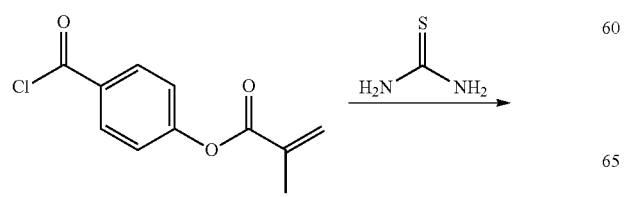
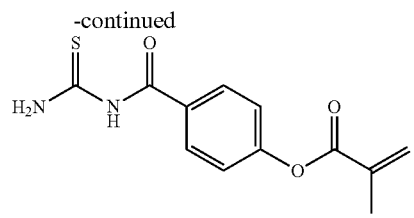
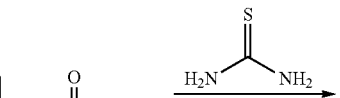
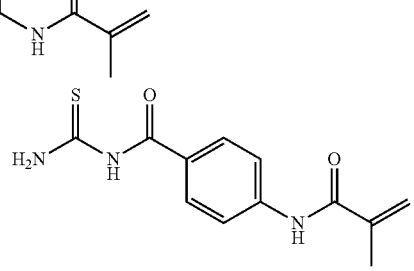
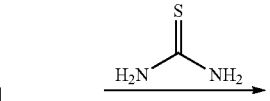
Polymerizable thiourea derivatives of Formula (I) preferred according to the invention are:
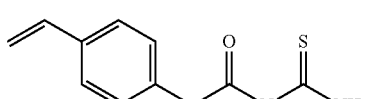
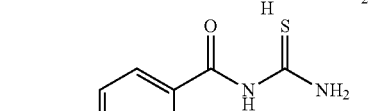
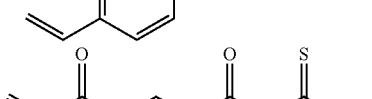
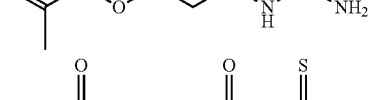
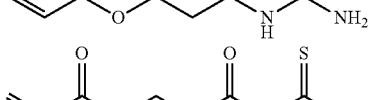
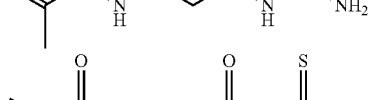

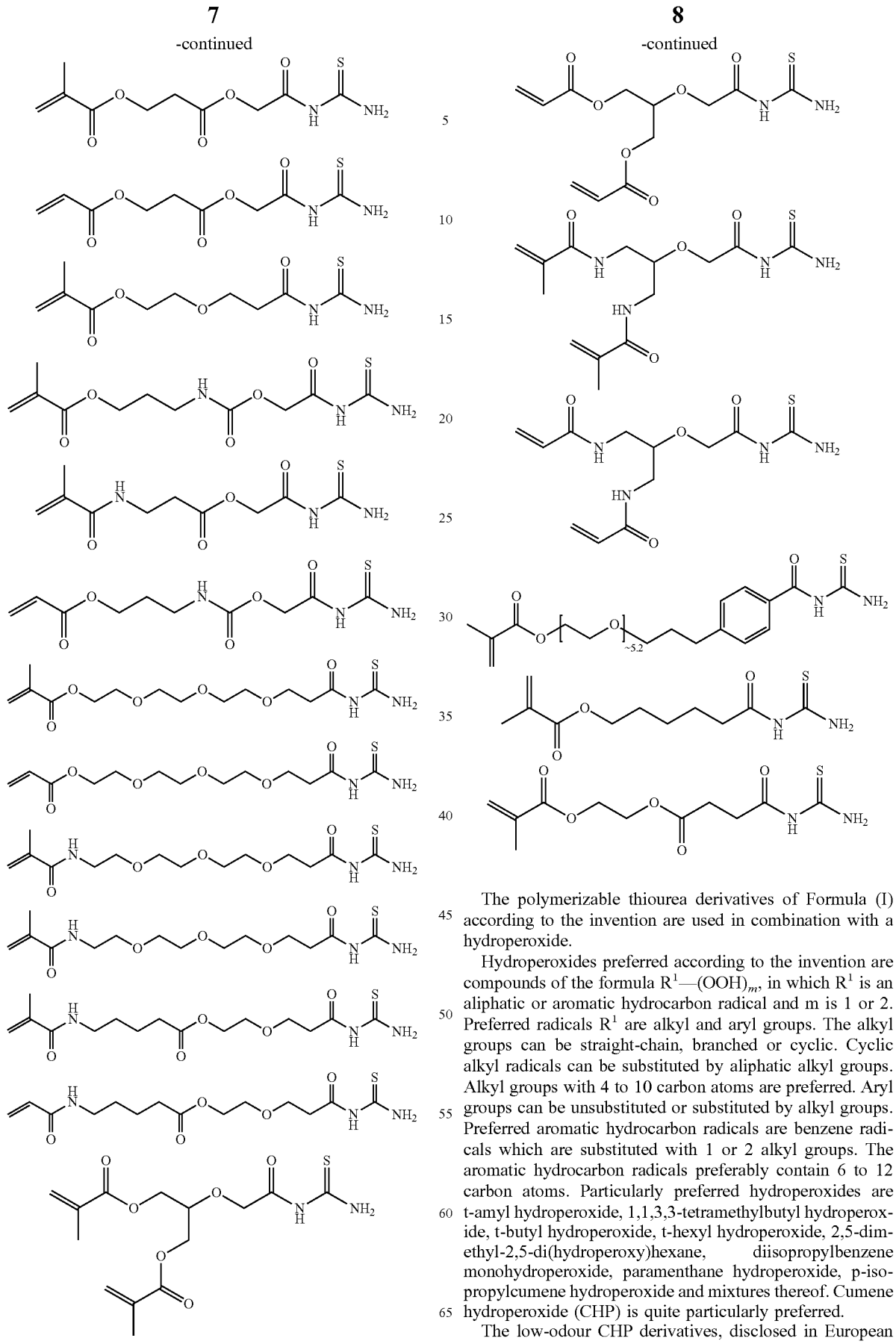

The polymerizable thiourea derivatives of Formula (I) according to the invention are used in combination with a hydroperoxide.

Hydroperoxides preferred according to the invention are compounds of the formula $R^1$—$(OOH)_m$, in which $R^1$ is an aliphatic or aromatic hydrocarbon radical and m is 1 or 2. Preferred radicals $R^1$ are alkyl and aryl groups. The alkyl groups can be straight-chain, branched or cyclic. Cyclic alkyl radicals can be substituted by aliphatic alkyl groups. Alkyl groups with 4 to 10 carbon atoms are preferred. Aryl groups can be unsubstituted or substituted by alkyl groups. Preferred aromatic hydrocarbon radicals are benzene radicals which are substituted with 1 or 2 alkyl groups. The aromatic hydrocarbon radicals preferably contain 6 to 12 carbon atoms. Particularly preferred hydroperoxides are t-amyl hydroperoxide, 1,1,3,3-tetramethylbutyl hydroperoxide, t-butyl hydroperoxide, t-hexyl hydroperoxide, 2,5-dimethyl-2,5-di(hydroperoxy)hexane, diisopropylbenzene monohydroperoxide, paramenthane hydroperoxide, p-isopropylcumene hydroperoxide and mixtures thereof. Cumene hydroperoxide (CHP) is quite particularly preferred.

The low-odour CHP derivatives, disclosed in European patent application EP 3 692 976 A1, of Formula II Formula II

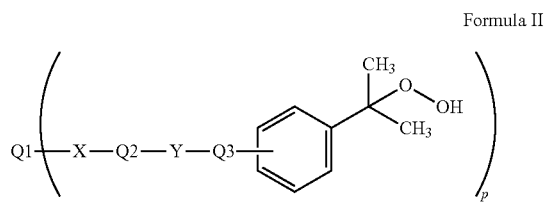

in which the variables have the following meanings:
$Q^1$ a p-valent, aromatic, aliphatic, linear or branched $C_1$-$C_{14}$ hydrocarbon radical, which can be interrupted by one or more S and/or O atoms and which can be unsubstituted or substituted by one or more substituents which are preferably selected from —OH, —OR$^2$, —Cl and —Br, wherein $R^2$ is an aliphatic, linear or branched $C_1$-$C_{10}$ hydrocarbon radical, X, Y independently of each other is in each case absent, —O—, —COO—; —CONR$^3$—, or —O—CO—NR$^4$—, wherein $R^3$ and $R^4$ independently of each other represent H or a $C_1$-$C_5$ alkyl radical, preferably H, methyl and/or ethyl, particularly preferably H, and wherein X and Y are preferably not absent at the same time, $Q^2$ is absent, an aliphatic, linear or branched $C_1$-$C_{14}$ alkylene radical, which can be interrupted by S and/or O atoms and which can be unsubstituted or substituted by —OH, —OR$^5$, —Cl and/or —Br, wherein $R^5$ is an aliphatic, linear or branched $C_1$-$C_{10}$ hydrocarbon radical, $Q^3$ a $C_1$-$C_3$ alkylene group or is absent, preferably —CH$_2$— or is absent, wherein X and/or Y is absent if $Q^2$ is absent, p 1, 2, 3 or 4, and wherein the substitution on the aromatic compound takes place in position 2, 3 or 4, relative to the cumene hydroperoxide group, are further preferred.

The variables preferably have the following meanings:
$Q^1$ a mono- or divalent, aliphatic, linear or branched $C_1$-$C_{10}$ hydrocarbon radical, which can be interrupted by one or more O atoms, preferably one O atom, and which can be substituted by one or more, preferably one, substituents which are selected from —OH and —OR$^2$ or is preferably unsubstituted, wherein $R^2$ is an aliphatic, linear or branched $C_1$-$C_6$ hydrocarbon radical, X, Y independently of each other is in each case absent, —O—, —COO— or —O—CO—NR$^4$—, wherein $R^4$ represents H or a $C_1$-$C_5$ alkyl radical, preferably H, methyl and/or ethyl and quite particularly preferably H, and wherein X and Y are preferably not absent at the same time, $Q^2$ is absent, a linear or branched $C_1$-$C_{10}$ alkylene radical, which can be interrupted by one or more O atoms, preferably one O atom, and which can be substituted by one or more, preferably one, substituents which are selected from —OH and —OR$^5$ or is preferably unsubstituted, wherein $R^5$ is an aliphatic, linear or branched $C_1$-$C_6$ hydrocarbon radical, p 1 or 2, and wherein the substitution on the aromatic compound takes place in position 3, preferably in position 4.

The variables particularly preferably have the following meanings:
$Q^1$ a mono- or divalent, aliphatic, linear or branched $C_1$-$C_5$ hydrocarbon radical, which can be interrupted by one O atom and which can be substituted by one OH group,

X —COO—,

Y is absent, $Q^2$ is absent or a linear $C_1$-$C_3$ alkylene radical, p 1 or 2, and wherein the substitution on the aromatic compound takes place in position 4.

The variables quite particularly preferably have the following meanings:
$Q^1$ a mono- or divalent, aliphatic, branched, preferably linear $C_1$-$C_4$ hydrocarbon radical,

X —COO—,

Y is absent, $Q^2$ is absent with or a methylene radical, p 1 or 2, and wherein the substitution on the aromatic compound takes place in position 4.

Hydroperoxide derivatives of Formula II preferred according to the invention are:

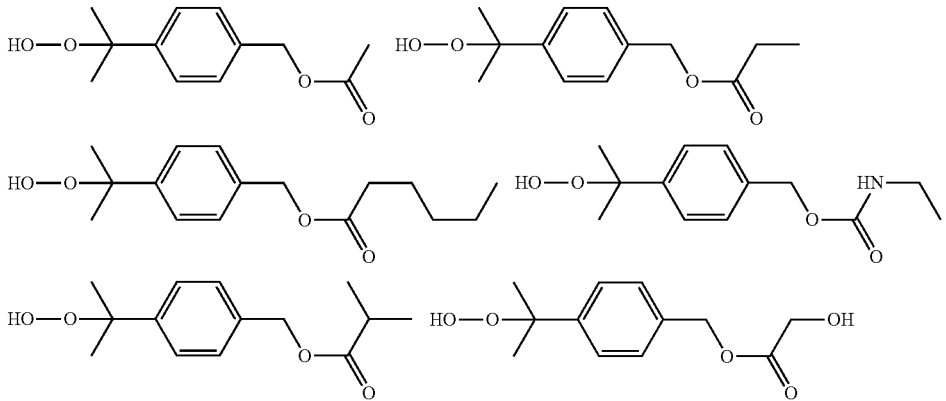

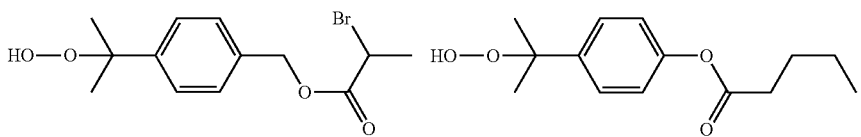

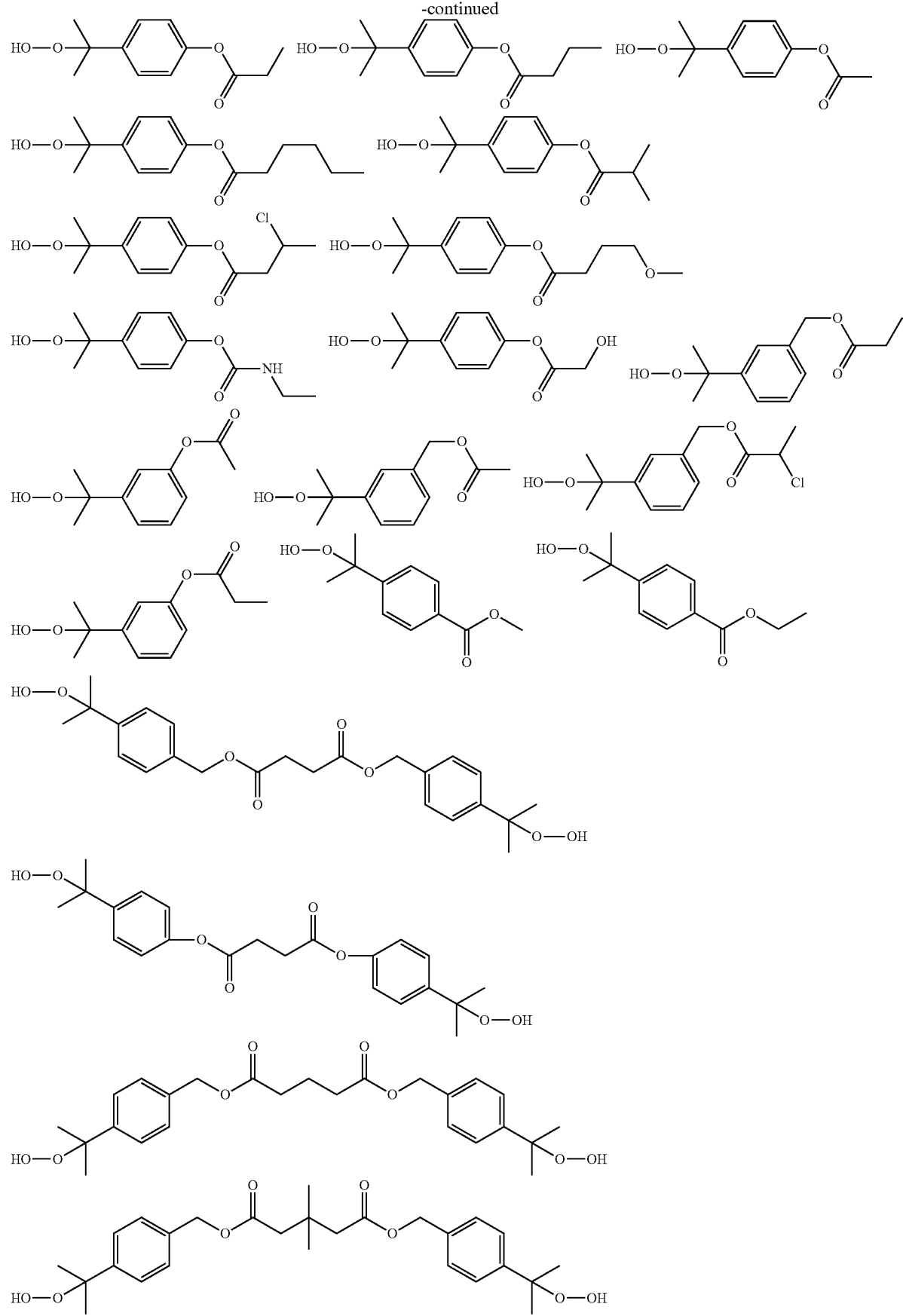

-continued
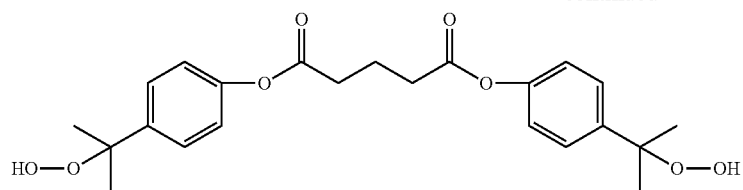
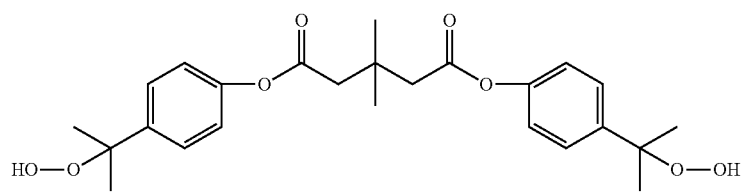
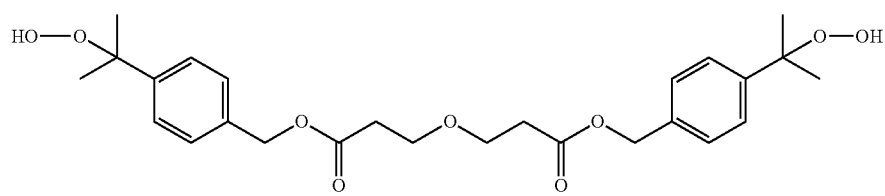
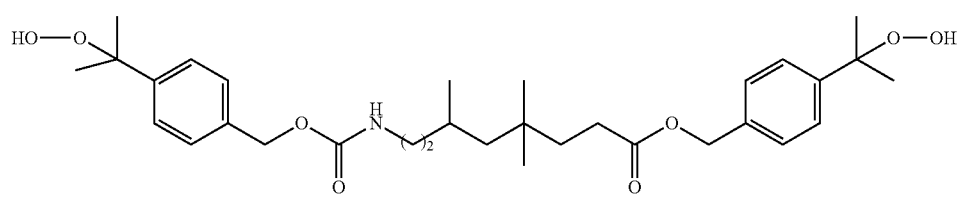
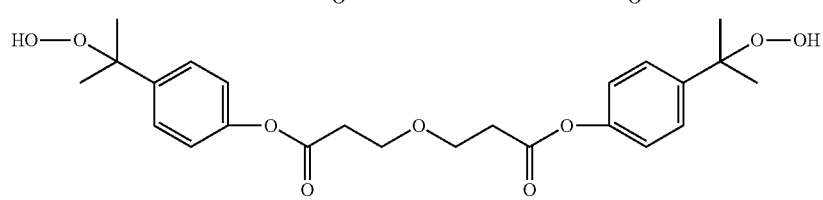
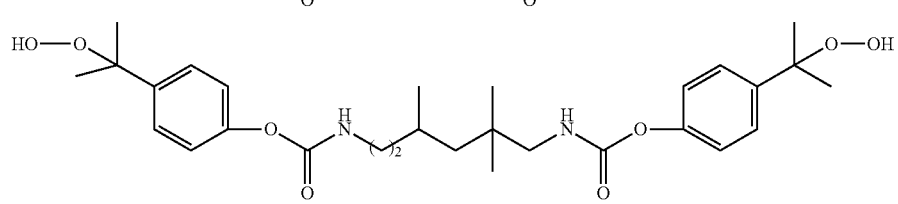
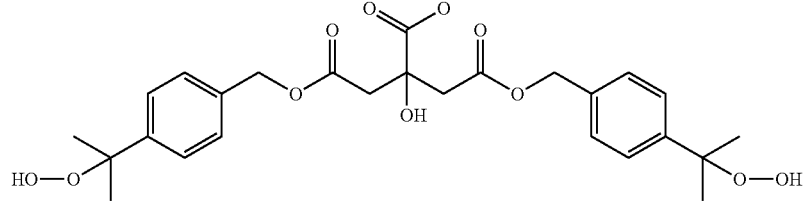

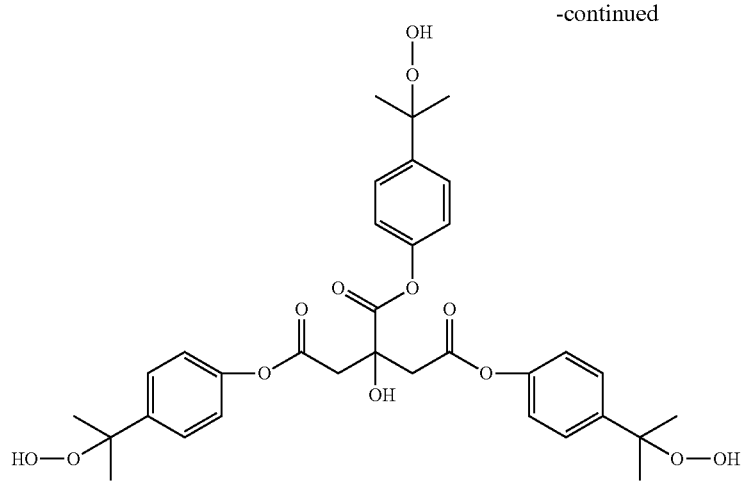

The hydroperoxide derivatives of Formula II display a great storage stability at room temperature and are particularly suitable as low-odour hydroperoxide component in redox initiator systems for dental compositions. The materials according to the invention can contain one or more hydroperoxides.

According to a further preferred embodiment the dental materials according to the invention additionally contain at least one transition metal compound in addition to at least one hydroperoxide and at least one thiourea derivative of Formula I. It has been found that the addition of a transition metal compound yields materials which have significantly improved mechanical properties after hardening.

Transition metal compounds preferred according to the invention are compounds which are derived from transition metals which have at least two stable oxidation states. Compounds of the elements copper, iron, cobalt, nickel and manganese are particularly preferred. These metals have the following stable oxidation states: Cu(I)/Cu(II), Fe(II)/Fe(III), Co(II)/Co(III), Ni(II)/Ni(III), Mn(II)/Mn(III). Materials which contain at least one copper compound are particularly preferred.

The transition metals are preferably used in the form of their salts. Preferred salts are the nitrates, acetates, 2-ethylhexanoates and halides, wherein chlorides are particularly preferred.

The transition metals can furthermore advantageously be used in complexed form, wherein complexes with chelate-forming ligands are particularly preferred. Preferred simple ligands for complexing the transition metals are 2-ethylhexanoate and THF. Preferred chelate-forming ligands are 2-(2-aminoethylamino)ethanol, aliphatic amines, particularly preferably 1,1,4,7,10,10-hexamethyltriethylenetetramine (HMTETA), N,N,N',N'',N''-pentamethyldiethylenetriamine (PMDETA), tris[2-(dimethylamino)ethyl]amine (Me$_6$TREN), N,N,N',N'-tetramethylethylenediamine (TMEDA), 1,4,8,11-tetraaza-1,4,8,11-tetramethylcyclotetradecane (Me4CYCLAM), diethylenetriamine (DETA), triethylenetetramine (TETA) and 1,4,8,11-tetraazacyclotetradecane (CYCLAM); pyridine-containing ligands, particularly preferably N,N,N',N'-tetrakis(2-pyridylmethyl)ethylenediamine (TPEN), N,N-bis(2-pyridylmethyl)amine (BPMA), N,N-bis(2-pyridylmethyl)octylamine (BPMOA), 2,2'-bipyridine and 8-hydroxyquinoline. Quite particularly preferred ligands are acetylacetone, dimethylglyoxime and 1,10-phenanthroline.

In the case of electrically neutral ligands, the charge of the transition metal ions must be balanced by suitable counterions. For this, the above-named ions which are used to form salts are considered in particular, wherein acetates and chlorides are particularly preferred. Chlorides and complexes are characterized by a relatively good solubility in monomers which are used to prepare dental materials.

Instead of the transition metal complexes, non-complex salts of the transition metals in combination with complex-forming organic compounds can be used to prepare the dental materials, preferably in combination with the above-named chelate-forming compounds. The organic ligands form the catalytically active complexes when mixed with the transition metal salts. The use of such combinations of transition metal salts and organic ligands is preferred.

Transition metal compounds of the metals copper, preferably $Cu^+$, iron, preferably $Fe^{3+}$, cobalt, preferably $Co^{3+}$, and nickel, preferably $Ni^{2+}$, are preferred.

Preferred copper salts are Cu(II) carboxylates (e.g. of acetic acid or 2-ethylhexanoic acid), $CuCl_2$, $CuBr_2$, $CuI_2$, particularly preferably CuBr and quite particularly preferably CuCl. Preferred copper complexes are complexes with the ligands acetylacetone, phenanthroline (e.g. 1,10-phenanthroline (phen)), aliphatic amines, such as e.g. 1,1,4,7,10,10-hexamethyltriethylenetetramine (HMTETA), N,N,N',N'',N''-pentamethyldiethylenetriamine (PMDETA), tris[2-(dimethylamino)ethyl]amine (Me$_6$TREN).

Preferred iron salts are $FeCl_3$, $FeBr_2$ and $FeCl_2$. Preferred iron complexes are complexes with the ligands acetylacetone, triphenylphosphine, 4,4'-di(5-nonyl)-2,2'-bipyridine (dNbpy) or 1,3-diisopropyl-4,5-dimethylimidazol-2-ylidene (Prilm). The complexes $Fe(acac)_2$ and $FeCl_2(PPh_3)_2$ are quite particularly preferred.

Preferred nickel salts are $NiBr_2$ and $NiCl_2$, preferred nickel complexes are nickel acetylacetonate and $NiBr_2(PPh_3)_2$.

According to the invention, copper compounds, copper complexes and in particular mixtures of copper salts and complexing organic ligands are particularly preferred. Salts and complexes of monovalent copper ($Cu^+$) are quite particularly preferred, copper(I) chloride (CuCl) is most preferred. Compositions which contain a salt of monovalent copper and in particular CuCl are characterized by a particularly good storage stability.

The materials according to the invention preferably contain 0.001 to 5 wt.-%, particularly preferably 0.005 to 3.0 wt.-% and quite particularly preferably 0.1 to 3.0 wt.-% at least one thiourea derivative of Formula (I).

The hydroperoxide or hydroperoxides are preferably used in a (total) quantity of from 0.01 to 5 wt.-%, particularly preferably 0.05 to 4.0 wt.-% and quite particularly preferably 0.1 to 3.0 wt.-%.

The transition metal compound is, where applicable, preferably used in a quantity of from 0.0001 to 1 wt.-%, preferably 0.0005 to 0.5 wt.-% and particularly preferably 0.0007 to 0.020 wt.-%.

Unless otherwise stated, all percentages herein relate to the total mass of the composition.

Thiourea derivatives of Formula (I) in combination with at least one hydroperoxide are particularly suitable for curing radically polymerizable compositions.

The materials according to the invention preferably contain at least one radically polymerizable monomer. Compositions which contain at least one mono- or multifunctional (meth)acrylate as radically polymerizable monomer are particularly preferred. By monofunctional (meth)acrylates is meant compounds with one, by multifunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates. Materials which are to be hardened intraorally preferably contain mono- and/or multifunctional methacrylates as radically polymerizable monomer.

Preferred mono- or multifunctional (meth)acrylates are methyl, ethyl, 2-hydroxyethyl, butyl, benzyl, tetrahydrofurfuryl or isobornyl (meth)acrylate, p-cumylphenoxyethylene glycol methacrylate (CMP-1 E), 2-(2-biphenyloxy)ethyl methacrylate, bisphenol A dimethacrylate, bis-GMA (an addition product of methacrylic acid and bisphenol A diglycidyl ether), ethoxylated or propoxylated bisphenol A dimethacrylate, such as e.g. 2-[4-(2-methacryloyloxyethoxyethoxy)phenyl]-2-[4-(2-methacryloyloxyethoxy)phenyl] propane) (SR-348c, from Sartomer; contains 3 ethoxy groups) and 2,2-bis[4-(2-methacryloxypropoxy)phenyl]propane, UDMA (an addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), di-, tri- or tetraethylene glycol dimethacrylate, trimethylolpropane trimethacrylate, pentaerythritol tetramethacrylate as well as glycerol di- and trimethacrylate, 1,4-butanediol dimethacrylate, 1,10-decanediol dimethacrylate (D3MA), bis(methacryloyloxymethyl)tricyclo-[5.2.1.0²,⁶]decane (DCP), polyethylene glycol or polypropylene glycol dimethacrylates, such as e.g. polyethylene glycol 200 dimethacrylate or polyethylene glycol 400 dimethacrylate (PEG 200 DMA or PEG 400 DMA) or 1,12-dodecanediol dimethacrylate, or a mixture thereof.

According to an embodiment the compositions according to the invention preferably additionally contain one or more acid-group-containing radically polymerizable monomers (adhesive monomers) in addition to the above-named monomers. These give the materials self-adhesive and/or self-etching properties. Acid-group-containing monomers are therefore particularly suitable for the preparation of self-adhesive dental materials, such as e.g. fixing cements.

Preferred acid-group-containing monomers are polymerizable carboxylic acids, phosphonic acids and phosphoric acid esters as well as their anhydrides. Preferred carboxylic acids and carboxylic acid anhydrides are 4-(meth)acryloyloxyethyl trimellitic acid anhydride, 10-methacryloyloxydecylmalonic acid, N-(2-hydroxy-3-methacryloyloxypropyl)-N-phenylglycine, 4-vinylbenzoic acid. Preferred phosphoric acid esters are 2-methacryloyloxyethylphenyl hydrogen phosphate, 10-methacryloyloxydecyl dihydrogen phosphate (MDP) and dipentaerythritol pentamethacryloyloxyphosphate. Preferred phosphonic acids are 4-vinylbenzylphosphonic acid, 2-[4-(dihydroxyphosphoryl)-2-oxabutyl]-acrylic acid and their amides, esters, such as e.g. 2-[4-(dihydroxyphosphoryl)-2-oxa-butyl]-acrylic acid-2,4,6-trimethylphenyl ester.

Particularly preferred acid-group-containing monomers are 4-vinylbenzylphosphonic acid, 2-[4-(dihydroxyphosphoryl)-2-oxa-butyl]-acrylic acid and their amides, esters, such as e.g. 2-[4-(dihydroxyphosphoryl)-2-oxa-butyl]-acrylic acid-2,4,6-trimethylphenyl ester, (meth)acrylamide dihydrogen phosphates, such as e.g. 6-methacrylamidohexyl or 1,3-bis(methacrylamido)-propan-2-yl dihydrogen phosphate, and mixtures thereof. These particularly preferred acid-group-containing monomers are characterized by a high hydrolytic stability.

The compositions according to the invention can advantageously additionally contain an initiator for the radical photopolymerization in addition to the initiator system according to the invention. Such compositions are dual-curing, i.e. they can be cured both chemically and by light. Preferred photoinitiators are benzophenone, benzoin as well as their derivatives, α-diketones and their derivatives, such as 9,10-phenanthrenequinone, 1-phenyl-propane-1,2-dione, diacetyl and 4,4'-dichlorobenzil. Camphorquinone (CQ) and 2,2-dimethoxy-2-phenyl-acetophenone are preferably used in combination with amines as reducing agent, such as e.g. ethyl-4-(dimethylamino) benzoate (EDMAB), or N,N-dimethylaminoethyl methacrylate.

Those compositions which do not contain amines are preferred according to the invention. Norrish type I photoinitiators are therefore particularly preferred. Norrish type I photoinitiators do not require an amine component.

Preferred Norrish type I photoinitiators are acyl- or bisacylphosphine oxides. Monoacyltrialkylgermanium, diacyldialkylgermanium and tetraacylgermanium compounds, such as e.g. benzoyltrimethylgermanium, dibenzoyldiethylgermanium, bis(4-methoxybenzoyl)diethylgermanium (Ivocerin®), tetrabenzoylgermanium and tetrakis(o-methylbenzoyl)germanium are particularly preferred.

Moreover, mixtures of the different photoinitiators can also be used, such as e.g. bis(4-methoxybenzoyl)diethylgermanium or tetrakis(o-methylbenzoyl)germanium in combination with camphorquinone and 4-dimethylaminobenzoic acid ethyl ester.

The dental materials according to the invention can moreover advantageously contain one or more organic or inorganic fillers. Particulate fillers are preferred. Filler-containing compositions are particularly suitable as dental fixing cements or filling composites.

Preferred inorganic fillers are oxides, such as $SiO_2$, $ZrO_2$ and $TiO_2$ or mixed oxides of $SiO_2$, $ZrO_2$, ZnO and/or $TiO_2$, nanoparticulate or microfine fillers, such as pyrogenic silica or precipitated silica, glass powders, such as quartz, glass ceramic, borosilicate or radiopaque glass powders, preferably barium or strontium aluminium silicate glasses, and radiopaque fillers, such as ytterbium trifluoride, tantalum(V) oxide, barium sulfate or mixed oxides of $SiO_2$ with ytterbium(III) oxide or tantalum(V) oxide. The dental materials according to the invention can furthermore contain fibrous fillers, nanofibres, whiskers or mixtures thereof. According to a preferred embodiment, the materials according to the invention do not contain fluoroaluminosilicate glasses, calcium aluminium silicate glasses or other fillers which react with organic acids in the sense of an acid-base reaction.

Preferably, the oxides have a particle size of from 0.010 to 15 µm, the nanoparticulate or microfine fillers have a particle size of from 10 to 300 nm, the glass powders have a particle size of from 0.01 to 15 µm, preferably of from 0.2 to 1.5 µm, and the radiopaque fillers have a particle size of from 0.2 to 5 µm.

Particularly preferred fillers are mixed oxides of $SiO_2$ and $ZrO_2$, with a particle size of from 10 to 300 nm, glass powders with a particle size of from 0.2 to 1.5 µm, in particular radiopaque glass powders of e.g. barium or strontium aluminium silicate glasses, and radiopaque fillers with a particle size of from 0.2 to 5 µm, in particular ytterbium trifluoride and/or mixed oxides of $SiO_2$ with ytterbium(III) oxide.

Moreover, ground prepolymers or pearl polymers (isofillers) are suitable as filler. These can consist exclusively of organic polymers, or of organic polymers which themselves are filled with inorganic fillers such as radiopaque glass powder(s) and ytterbium trifluoride. The above-defined monomers and fillers are suitable for the preparation of the ground prepolymers and pearl polymers. Compositions for the production of complete dentures preferably contain exclusively organic fillers, particularly preferably ground polymers or pearl polymers based on polymethyl methacrylate (PMMA), quite particularly preferably pearl polymers based on PMMA, as fillers. According to a preferred embodiment, the materials according to the invention do not contain polymers with acid groups, in particular polymers with carboxylic acid groups.

Unless otherwise stated, all particle sizes are weight-average particle sizes, wherein the particle-size determination in the range of from 0.1 µm to 1000 µm is effected by means of static light scattering, preferably using an LA-960 static laser scattering particle size analyzer (Horiba, Japan). Here, a laser diode with a wavelength of 655 nm and an LED with a wavelength of 405 nm are used as light sources. The use of two light sources with different wavelengths makes it possible to measure the entire particle-size distribution of a sample in only one measurement pass, wherein the measurement is carried out as a wet measurement. For this, a 0.1 to 0.5% aqueous dispersion of the filler is prepared and the scattered light thereof is measured in a flow cell. The scattered-light analysis for calculating particle size and particle-size distribution is effected in accordance with the Mie theory according to DIN/ISO 13320.

Particle sizes smaller than 0.1 µm are preferably determined by means of dynamic light scattering (DLS). The measurement of the particle size in the range of from 5 nm to 0.1 µm is preferably effected by dynamic light scattering (DLS) of aqueous particle dispersions, preferably with a Malvern Zetasizer Nano ZS (Malvern Instruments, Malvern UK) with an He—Ne laser with a wavelength of 633 nm, at a scattering angle of 90° at 25° C.

The light scattering decreases as the particle size decreases. Particle sizes smaller than 0.1 µm can also be determined by means of SEM or TEM spectroscopy. The transmission electron microscopy (TEM) is preferably carried out with a Philips CM30 TEM at an accelerating voltage of 300 kV. For the preparation of the samples, drops of the particle dispersion are applied to a 50 Å thick copper grid (mesh size 300), which is coated with carbon, and then the solvent is evaporated.

The fillers are divided according to their particle size into macrofillers and microfillers, wherein fillers with an average particle size of from 0.2 to 10 µm are called macrofillers and fillers with an average particle size of from approx. 5 to 100 nm are called microfillers. Macrofillers are obtained e.g. by grinding e.g. quartz, radiopaque glasses, borosilicates or ceramic and usually consist of splintery parts. Microfillers such as mixed oxides can be prepared e.g. by hydrolytic co-condensation of metal alkoxides. Fillers with a small particle size have a greater thickening action.

To improve the bond between the filler particles and the crosslinked polymerization matrix, the fillers are preferably surface-modified, particularly preferably by silanization, quite particularly preferably by radically polymerizable silanes, in particular with 3-methacryloyloxypropyltrimethoxysilane. For the surface modification of non-silicate fillers, e.g. of $ZrO_2$ or $TiO_2$, functionalized acidic phosphates, such as e.g. 10-methacryloyloxydecyl dihydrogen phosphate can also be used.

Moreover, the dental materials according to the invention can contain one or more further additives, above all stabilizers, colorants, microbiocidal active ingredients, fluoride-ion-releasing additives, foaming agents, optical brighteners, plasticizers and/or UV absorbers. The materials according to the invention can also contain one or more organic or inorganic solvents as additives. According to a preferred embodiment, the materials according to the invention do not, however, contain water.

Dental materials which contain
(a) 0.001 to 5.0 wt.-%, preferably 0.005 to 3.0 wt.-%, particularly preferably 0.1 to 3.0 wt.-% at least one thiourea derivative of Formula (I),
(b) 0.01 to 5.0 wt.-%, preferably 0.05 to 4.0 wt.-% and particularly preferably 0.1 to 3.0 wt.-% at least one hydroperoxide,
(c) 5 to 95 wt.-%, preferably 10 to 95 wt.-% and particularly preferably 10 to 90 wt.-% at least one radically polymerizable monomer,
(d) 0 to 80 wt.-% filler(s), and
(e) 0.01 to 5 wt.-%, preferably 0.1 to 3 wt.-% and particularly preferably 0.1 to 2 wt.-% additive(s)
are preferred according to the invention.

All quantities herein are relative to the total mass of the composition, unless otherwise stated.

The filling level is geared towards the desired intended use of the material. Preferably filling composites have a filler content of from 50 to 80 wt.-%, particularly preferably 70 to 80 wt.-%, and dental cements have a filler content of from 10 to 70 wt.-%, particularly preferably 60 to 70 wt.-%. Prosthesis materials preferably have a filler content of from 0 to 10 wt.-%, particularly preferably 0 to 5 wt.-%.

Dental materials which additionally contain
(f) 0.0001 to 1 wt.-%, preferably 0.0005 to 0.5 wt.-%, particularly preferably 0.0007 to 0.02 wt.-% of at least one transition metal compound
are particularly preferred.

Those dental materials which consist of the named components are particularly preferred, wherein the individual components are preferably in each case selected from the above-named preferred and particularly preferred substances. In all cases, a mixture of several substances, thus for example a mixture of monomers, can also be used as respective component.

The materials according to the invention are preferably present in the form of two separate components, of which the first component contains the hydroperoxide (catalyst paste) and the second component contains the thiourea derivative (base paste). As the components preferably have a paste-like consistency, they are also called pastes herein.

The composition of catalyst and base pastes essentially differs in that the catalyst paste contains one or more hydroperoxides and the base paste contains one or more thiourea derivatives.

The pastes are mixed with each other for use and the hardening reaction is initiated hereby. The pastes are preferably blended such that catalyst and base pastes can be used in a volume ratio of 1:1. After mixing the pastes, the materials have the above-defined composition.

The dental materials according to the invention are characterized in particular in that they do not have a bitter taste after hardening. Moreover, they have good curing characteristics, i.e. they have an advantageous processing time in combination with an advantageous curing time. Furthermore, after hardening, the materials have mechanical properties which are comparable with materials based on established redox systems, such as e.g. a mixture of acetyl thiourea and cumene hydroperoxide (CHP), without restrictions.

The compositions according to the invention are particularly suitable as dental materials, in particular as dental cements, filling composites and veneering materials as well as materials for the production of prostheses, artificial teeth, inlays, onlays, crowns and bridges. The compositions are suitable primarily for intraoral application by the dentist for the restoration of damaged teeth, i.e. for therapeutic application, e.g. as dental cements, filling composites and veneering materials. However, they can also be used non-therapeutically (extraorally), for example in the production or repair of dental restorations, such as prostheses, artificial teeth, inlays, onlays, crowns and bridges.

The invention is explained in more detail in the following with reference to embodiment examples:

EXAMPLES

Example 1

Synthesis of N-(2-methacryloyloxyhexanoyl)-thiourea

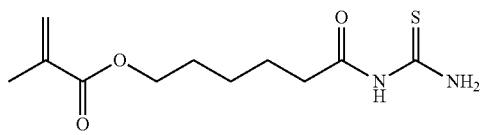 [SMILES: C=C(C)C(=O)OCCCCCC(=O)NC(N)=S]

1st Stage: 6-Hydroxyhexanoic acid tert.-butyl ester

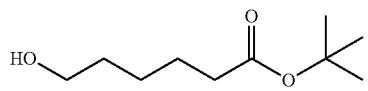

ε-Caprolactone (181.88 g, 1.59 mol) was dissolved in tert.-butanol (1600 ml). Potassium tert.-butoxide (196.68 g, 1.75 mol) was added and the suspension was heated at reflux for 5 h. After cooling, toluene (1600 ml) and water (800 ml) were added, and the phases were separated. The organic phase was washed with water (2×1000 ml) and saturated aqueous sodium chloride solution (1000 ml), dried over anhydrous sodium sulfate, filtered and concentrated on a rotary evaporator. The crude product was purified by means of vacuum distillation (boiling point: 70° C./0.03 mbar). 56.57 g (0.30 mol; 19% yield) of a colourless liquid was obtained.

$^1$H-NMR (CDCl$_3$, 400 MHz): δ=3.63 (t, 2H; J=6.6 Hz; O—CH$_2$), 2.67 (d, 1H; J=0.8 Hz; OH), 2.22 (t, 2H; J=7.4 Hz; (C=O)CH$_2$), 1.63-1.56 (m, 4H; CH$_2$), 1.44 (s, 9H; CH$_3$), 1.43-1.34 (m, 2H; CH$_2$).

$^{13}$C-NMR (CDCl$_3$, 100.6 MHz): δ=173.2 (C=O), 80.0 (C), 62.3 (CH$_2$), 35.4 (CH$_2$), 32.2 (CH$_2$), 28.0 (CH$_3$), 25.1 (CH$_2$), 24.6 (CH$_2$).

2nd Stage: 6-Methacryloyloxyhexanoic acid tert.-butyl ester

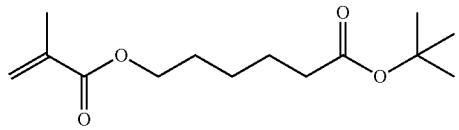 [SMILES: C=C(C)C(=O)OCCCCCC(=O)OC(C)(C)C]

A solution of 6-hydroxyhexanoic acid tert.-butyl ester (11.15 g, 59.2 mmol), triethylamine (7.18 g, 71.0 mmol) and N,N-dimethylaminopyridine (0.36 g, 3.0 mmol) in toluene (50 ml) was cooled to 0° C. A solution of methacrylic acid anhydride (10.95 g, 71.0 mmol) in toluene (10 ml) was added dropwise, and the reaction mixture was stirred for 1 h at 0° C. and for 1 h at ambient temperature. The reaction solution was washed with hydrochloric acid (1N, 3×100 ml), sodium hydroxide solution (1N, 3×100 ml), water (2×100 ml) and saturated aqueous sodium chloride solution (100 ml), dried over anhydrous sodium sulfate, filtered and concentrated on a rotary evaporator. 14.35 g (56.0 mmol; 95% yield) of a colourless liquid was obtained.

$^1$H-NMR (CDCl$_3$, 400 MHz): δ=6.09 (m, 1H; =CH), 5.54 (m, 1H; =CH), 4.15 (t, 2H; J=6.5 Hz; O—CH$_2$), 2.23 (t, 2H; J=7.4 Hz; (C=O)CH$_2$), 1.94 (m, 3H; CH$_3$), 1.74-1.60 (m, 4H; CH$_2$), 1.44 (s, 9H; CH$_3$), 1.43-1.37 (m, 2H; CH$_2$).

$^{13}$C-NMR (CDCl$_3$, 100.6 MHz): δ=172.8 (C=O), 167.3 (C=O), 136.4 (=C), 125.1 (=CH$_2$), 79.9 (C), 64.4 (CH$_2$), 35.3 (CH$_2$), 28.2 (CH$_2$), 28.0 (CH$_3$), 25.4 (CH$_2$), 24.6 (CH$_2$), 18.2 (CH$_3$).

3rd Stage: 6-Methacryloyloxyhexanoic acid

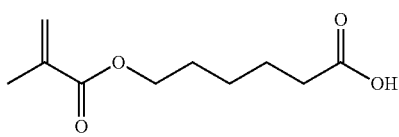

6-Methacryloyloxyhexanoic acid tert.-butyl ester (8.79 g, 34.3 mmol) was dissolved in dichloromethane (100 ml), and trifluoroacetic acid (20 ml) was added. The reaction mixture was stirred at ambient temperature. After 18 h the solution was concentrated on a rotary evaporator. Trifluoroacetic acid residues were removed by means of azeotropic distillation with toluene, and 6.87 g (34.3 mmol; 100% yield) of a slightly yellowish liquid was obtained.

$^1$H-NMR (CDCl$_3$, 400 MHz): δ=11.40 (br s, 1H; OH), 6.10 (m, 1H; =CH), 5.56 (m, 1H; =CH), 4.16 (t, 2H; J=6.5

Hz; O—CH$_2$), 2.39 (t, 2H; J=7.4 Hz; (C=O)CH$_2$), 1.94 (m, 3H; CH$_3$), 1.76-1.66 (m, 4H; CH$_2$), 1.49-1.41 (m, 2H; CH$_2$).

$^{13}$C-NMR (CDCl$_3$, 100.6 MHz): δ=179.7 (C=O), 167.6 (C=O), 136.2 (=C), 125.4 (=CH$_2$), 64.4 (CH$_2$), 33.7 (CH$_2$), 28.1 (CH$_2$), 25.3 (CH$_2$), 24.1 (CH$_2$), 18.1 (CH$_3$).

4th Stage: 6-Methacryloyloxyhexanoic acid chloride

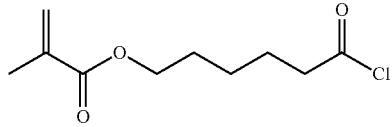

Oxalic acid dichloride (5.15 g, 40.6 mmol) was added dropwise to a solution of 6-methacryloyloxyhexanoic acid (6.77 g, 33.8 mmol) and N,N-dimethylformamide (0.1 ml) in dichloromethane (100 ml). The reaction solution was stirred for 3 h at ambient temperature and then concentrated on a rotary evaporator. 7.18 g (32.8 mmol; 97% yield) of a yellowish liquid was obtained.

$^1$H-NMR (CDCl$_3$, 400 MHz): δ=6.08 (m, 1H; =CH), 5.56 (m, 1H; =CH), 4.15 (t, 2H; J=6.5 Hz; O—CH$_2$), 2.93 (t, 2H; J=7.4 Hz; (C=O)CH$_2$), 1.94 (m, 3H; CH$_3$), 1.80-1.68 (m, 4H; CH$_2$), 1.50-1.43 (m, 2H; CH$_2$).

$^{13}$C-NMR (CDCl$_3$, 100.6 MHz): δ=173.4 (C=O), 167.2 (C=O), 136.2 (=C), 125.2 (=CH$_2$), 64.0 (CH$_2$), 46.7 (CH$_2$), 28.0 (CH$_2$), 24.7 (CH$_2$), 24.5 (CH$_2$), 18.1 (CH$_3$).

5th Stage: N-(2-Methacryloyloxyhexanoyl)-thiourea

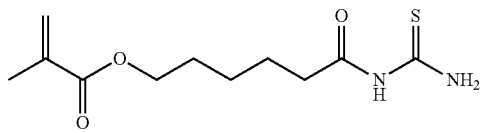 [SMILES: C=C(C)C(=O)OCCCCCC(=O)NC(N)=S]

6-Methacryloyloxyhexanoic acid chloride (7.05 g, 32.2 mmol) was dissolved in toluene (80 ml). Thiourea (2.70 g, 35.5 mmol) was added, and the suspension was heated at reflux for 3 h. After cooling, the suspension was filtered. The filtration residue was washed with toluene (100 ml) and dried, suspended in water (100 ml), filtered, washed with water (2×50 ml) and dried. The yellowish solid was dissolved in toluene (50 ml) at 60° C. The solution was cooled to 0° C. and cold filtered. The filtration residue was washed with cold toluene (2×10 ml) and dried. 1.18 g (4.6 mmol; 14% yield) of a white solid (m.p.: 97° C.) was obtained.

$^1$H-NMR (CDCl$_3$, 400 MHz): δ=9.95 (br s, 1H; NH), 9.61 (br s, 1H; NH), 7.54 (br s, 1H; NH), 6.10 (s, 1H; =CH), 5.56 (s, 1H; =CH), 4.16 (t, 2H; J=6.5 Hz; O—CH$_2$), 2.41 (t, 2H; J=7.4 Hz; (C=O)CH$_2$), 1.94 (s, 3H; CH$_3$), 1.77-1.64 (m, 4H; CH$_2$), 1.50-1.39 (m, 2H; CH$_2$).

$^{13}$C-NMR (CDCl$_3$, 100.6 MHz): δ=182.0 (C=S), 173.8 (C=O), 167.5 (C=O), 136.3 (=C), 125.4 (=CH$_2$), 64.2 (CH$_2$), 36.8 (CH$_2$), 28.1 (CH$_2$), 25.3 (CH$_2$), 24.1 (CH$_2$), 18.2 (CH$_3$).

Example 2

Synthesis of N-(4-vinylbenzoyl)-thiourea

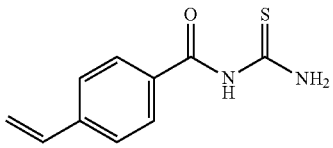

1st Stage: 4-Vinylbenzoyl chloride

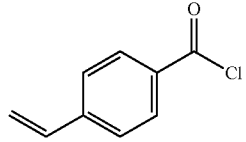

Dichloromethane (100 ml) and N,N-dimethylformamide (0.1 ml) were added to 4-vinylbenzoic acid (16.00 g, 0.108 mol) and oxalic acid dichloride (16.45 g, 0.130 mol) was added dropwise. The reaction mixture was stirred for 4 h at RT and then filtered over silica gel. The filtrate was concentrated on a rotary evaporator, and 16.51 g (99.0 mmol; 92%) of a slightly brownish liquid was obtained.

$^1$H-NMR (CDCl$_3$, 400 MHz): δ=8.05 (d, 2H; J=8.5 Hz; Ar—H), 7.50 (d, 2H; J=8.4 Hz; Ar—H), 6.75 (dd, 1H; J=10.9 Hz, 17.6; =CH), 5.93 (d, 1H; J=17.6; =CH), 5.48 (d, 1H; J=10.9; =CH).

$^{13}$C-NMR (CDCl$_3$, 100.6 MHz): δ=167.8 (C=O), 144.3 (Ar—C), 135.3 (=CH), 132.0 (Ar—C), 131.8 (Ar—CH), 126.5 (Ar—CH), 118.4 (=CH$_2$).

2nd Stage: N-(4-Vinylbenzoyl)-thiourea

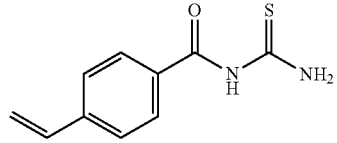

4-Vinylbenzoyl chloride (16.41 g, 98.5 mmol) was dissolved in toluene (150 ml) and thiourea (8.25 g, 0.108 mol) was added. The suspension was heated at reflux for 5 h and filtered after cooling. The filtration residue was washed with toluene (100 ml), water (300 ml) was added, and heated to 60° C. After cooling, the suspension was filtered. The filtration residue was washed with water (5×100 ml) and dried. Dichloromethane (500 ml) was added to the yellowish solid, and it was heated at reflux. The suspension was filtered. The filtrate was concentrated on a rotary evaporator. The yellowish solid was dissolved in ethyl acetate (100 ml) and filtered over silica gel. The filtrate was concentrated on a rotary evaporator, and 3.90 g (18.9 mmol; 19%) of a white solid was obtained.

$^1$H-NMR (DMSO-d$_6$, 400 MHz): δ=11.25 (s, 1H; NH), 9.91 (s, 1H; NH), 9.60 (s, 1H; NH), 7.95 (d, 2H; J=8.4 Hz;

Ar—H), 7.61 (d, 2H; J=8.4 Hz; Ar—H), 6.82 (dd, 1H; J=10.9 Hz, 17.7; =CH), 6.02 (d, 1H; J=17.5; =CH), 5.44 (d, 1H; J=11.2; =CH).

$^{13}$C-NMR (DMSO-d$_6$, 100.6 MHz): δ=182.5 (C=S), 167.8 (C=O), 141.9 (m, Ar—C), 136.9 (m, =CH), 135.4 (m, Ar—C), 131.7-125.3 (m, Ar—CH), 119.4-116.2 (m, =CH$_2$).

Example 3

N-(2-Methacryloyloxyethoxysuccinoyl)-thiourea

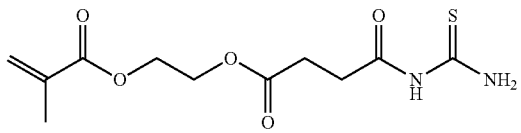 [SMILES: C=C(C)C(=O)OCCOC(=O)CCC(=O)NC(N)=S]

1st Stage:
3-(2-Methacryloyloxyethyloxycarbonyl)propionic acid chloride

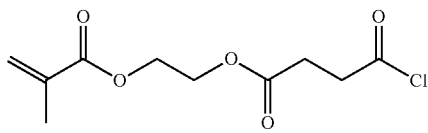 [SMILES: C=C(C)C(=O)OCCOC(=O)CCC(=O)Cl]

Succinic acid mono(methacryloyloxyethyl) ester (11.51 g, 50.0 mmol) was dissolved in dichloromethane (80 ml). N,N-Dimethylformamide (0.1 ml) was added, and oxalic acid dichloride (6.35 g, 50.0 mmol) was added dropwise. The reaction solution was stirred for 3 h at ambient temperature and then concentrated on a rotary evaporator. 12.39 g (49.8 mmol; 100%) of a colourless liquid was obtained.

$^1$H-NMR (CDCl$_3$, 400 MHz): δ=6.03 (s, 1H; =CH), 5.61 (s, 1H; =CH), 4.37 (s, 4H; OCH$_2$), 3.23 (t, 2H; J=6.5 Hz; CH$_2$), 2.72 (t, 2H; J=6.5 Hz; CH$_2$), 1.95 (s, 3H; CH$_3$).

$^{13}$C-NMR (CDCl$_3$, 100.6 MHz): δ=172.8 (C=O), 170.5 (C=O), 166.9 (C=O), 135.7 (=C), 126.1 (=CH$_2$), 62.7 (O—CH$_2$), 62.0 (O—CH$_2$), 41.5 (CH$_2$), 29.1 (CH$_2$), 18.1 (CH$_3$).

2nd Stage:
N-(2-Methacryloyloxyethoxysuccinoyl)-thiourea

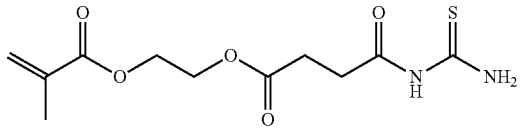 [SMILES: C=C(C)C(=O)OCCOC(=O)CCC(=O)NC(N)=S]

3-(2-Methacryloyloxyethyloxycarbonyl)propionic acid chloride (12.43 g, 50.0 mmol) was dissolved in toluene (100 ml). Thiourea (4.19 g, 55.0 mmol) was added, and the suspension was heated at reflux for 2 h. After cooling, the suspension was filtered. The filtration residue was washed with toluene (100 ml) and dried, and 2.44 g (8.4 mmol; 17%) of a white solid (melting point: 151° C.) was obtained.

$^1$H-NMR (DMSO-d$_6$, 400 MHz): δ=11.18 (s, 1H; NH), 9.53 (s, 1H; NH), 9.35 (s, 1H; NH), 6.03 (m, 1H; =CH), 5.69 (m, 1H; =CH), 4.28 (s, 4H; O—CH$_2$), 2.71-2.54 (m, 4H; CH$_2$), 1.88 (s, 3H; CH$_3$).

$^{13}$C-NMR (DMSO-d$_6$, 100.6 MHz): δ=182.0 (C=S), 173.7 (C=O), 172.4 (C=O), 166.8 (m, C=O), 135.6 (m, =C), 128.0 (m, =CH$_2$), 126.4 (m, =CH$_2$), 62.6 (m, O—CH$_2$), 30.0 (m, N—CH$_2$), 17.7 (CH$_3$).

Example 4 (Comparison Example)

Synthesis of methacrylic acid 4-oxo-9-thioxo-5-oxa-3,8,10-triazatridec-12-en-1-yl ester

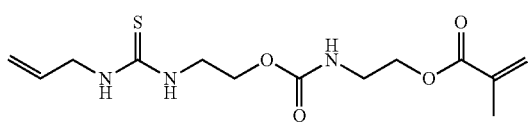 [SMILES: C=CCNC(=S)NCCOC(=O)NCCOC(=O)C(=C)C]

N-Allyl-N'-(2-hydroxyethyl)thiourea (8.01 g, 50.0 mmol) was dissolved in anhydrous tetrahydrofuran (80 ml) and isocyanatoethyl methacrylate (7.76 g, 50.0 mmol) was added dropwise. Dibutyltin dilaurate (0.24 g, 2.0 mmol) was added and the reaction mixture was stirred at RT. After 20 h the clear colourless solution was concentrated on a rotary evaporator. The colourless oil was dissolved in ethyl acetate (50 ml) and filtered over silica gel. The filtrate was concentrated on a rotary evaporator, and 15.45 g (48.9 mmol; 98%) of a waxy white solid was obtained.

$^1$H-NMR (CDCl$_3$, 400 MHz): δ=7.04-6.65 (m, 2H; NH), 6.13 (s, 1H; =CH), 5.92-5.80 (m, 1H; =CH), 5.62 (s, 1H; =CH), 5.60-5.49 (m, 1H; NH), 4.34-4.19 (m, 4H; CH$_2$), 4.19-3.64 (m, 4H; CH$_2$), 3.54-3.32 (m, 2H; N—CH$_2$), 1.95 (s, 3H; CH$_3$).

$^{13}$C-NMR (CDCl$_3$, 100.6 MHz): δ=182.0 (C=S), 167.3 (C=O), 156.7 (C=O), 135.6 (=C), 133.1 (=CH), 126.2 (=CH$_2$), 117.0 (=CH$_2$), 63.3 (m, O—CH$_2$), 63.2 (m, O—CH$_2$), 46.4 (N—CH$_2$), 44.4 (N—CH$_2$), 40.1 (N—CH$_2$), 18.1 (CH$_3$).

Example 5

Composite Cements Based on Thioureas According to the Invention

Chemically curing composite cements, in each case consisting of a base paste and a catalyst paste, were prepared from a mixture of the dimethacrylates UDMA (addition product of 2-hydroxyethyl methacrylate and 2,2,4-trimethylhexamethylene-1,6-diisocyanate), bis-GMA (an addition product of methacrylic acid and bisphenol A diglycidyl ether) and 2-(2-biphenyloxy)-ethyl methacrylate (MA-836) as well as the stabilizers MEHQ (hydroquinone monomethyl ether) and TEMPO (2,2,6,6-tetramethyl piperidin-1-yl) oxyl), the filler GM27884 0.7 μm sil. (silanized glass filler GM G018-056, average particle size 0.7 μm, Schott) as well as the initiator components CHP (cumene hydroperoxide, 80%), copper(II) acetylacetonate (Cu(acac)$_2$) and in each case a thiourea compound.

TABLE 1

Composition of the catalyst paste Cat-1

| Component | Proportion (wt.-%) |
|---|---|
| Bis-GMA | 10.020 |
| UDMA | 13.352 |
| MA-836 | 10.020 |
| CHP | 1.590 |
| MEHQ | 0.018 |
| GM27884 0.7 um sil. | 65.000 |
| Total | 100.00 |

TABLE 2

Composition of the base pastes

| Component | Base 1*) | Base 2 | Base 3 | Base 4*) | Base 5*) |
|---|---|---|---|---|---|
| Bis-GMA | 10.244 | 10.118 | 10.192 | 10.319 | 10.034 |
| UDMA | 13.663 | 13.515 | 13.613 | 13.785 | 13.414 |
| MA-836 | 10.244 | 10.118 | 10.192 | 10.319 | 10.034 |
| Hexanoyl thiourea | 0.820 | 0 | 0 | 0 | 0 |
| N-(2-Methacryloyloxyhexanoyl)-thiourea (from Example 1) | 0 | 1.220 | 0 | 0 | 0 |
| N-(4-Vinylbenzoyl)-thiourea (from Example 2) | 0 | 0 | 0.974 | 0 | 0 |
| Allyl thiourea | 0 | 0 | 0 | 0.548 | 0 |
| Methacrylic acid 4-oxo-9-thioxo-5-oxa-3,8,10-triazatridec-12-en-1-yl ester (from Example 4) | 0 | 0 | 0 | 0 | 1.489 |
| Cu(acac)$_2$ | 0.004 | 0.004 | 0.004 | 0.004 | 0.004 |
| MEHQ | 0.018 | 0.018 | 0.018 | 0.018 | 0.018 |
| TEMPO | 0.007 | 0.007 | 0.007 | 0.007 | 0.007 |
| GM27884 0.7 um sil. | 65.000 | 65.000 | 65.000 | 65.000 | 65.000 |
| Total | 100.00 | 100.00 | 100.00 | 100.00 | 100.00 |

*)Comparison example

The catalyst paste Cat-1 was blended with the various base pastes in a 1:1 volume ratio and the processing time of the cements obtained was determined. The processing time (PT) of the paste mixtures was determined by means of a rheometer (Motion Compact Rheometer MCR 302, Anton Paar). For this, the catalyst paste and the base pastes were blended by hand on a mixing block in a 1:1 ratio. The material was then applied to a die, consisting of Delrin, with a roughened surface on the rheometer. A measuring bob shaft secured on a spindle with a likewise roughened surface compresses the sample and with slight rotation determines the storage modulus. At the beginning of the stable phase and after reaching a particular gradient, an inflection point was defined in each case. The inflection points were then connected by a straight line. The measurement point furthest away from this straight line was defined as PT. The whole measurement was carried out at 28.7° C. in a temperature-controlled chamber. The results are specified in Table 3.

TABLE 3

Processing times (PT) of the cements

| Cement | Thiourea derivative | PT at 28.7° C. [s] |
|---|---|---|
| Cat-1 + Base 1*) | Hexanoyl thiourea | 123 ± 3 |
| Cat-1 + Base 2 | N-(2-Methacryloyloxyhexanoyl)-thiourea (from Example 1) | 151 ± 4 |
| Cat-1 + Base 3 | K247 N-(4-Vinylbenzoyl)-thiourea (from Example 2) | 360 ± 1 |
| Cat-1 + Base 4*) | Allyl thiourea | 242 ± 1 |
| Cat-1 + Base 5*) | Methacrylic acid 4-oxo-9-thioxo-5-oxa-3,8,10-triazatridec-12-en-1-yl ester (from Comparison Example 4) | 478 ± 20 |

*)Comparison example

The flexural strength and the flexural modulus of elasticity of the cements were determined according to the EN ISO-4049 standard (Dentistry—Polymer-based filling, restorative and luting materials). For this, the catalyst paste Cat-1 was blended with the various base pastes, in each case in a 1:1 volume ratio, and test pieces in accordance with the standard were prepared from the mixture. These were cured by storage in a heating cabinet at 37° C. for 45 minutes and the mechanical properties were then measured. The results are collated in Table 4.

The results prove that, after hardening, the composite cements according to the invention have much better mechanical properties than comparative materials with known polymerizable thiourea derivatives, which are comparable with the mechanical properties of cements based on the tried and tested initiator system of CHP with hexanoyl thiourea in every respect.

TABLE 4

Flexural strength (FS, MPa) and flexural modulus of elasticity (FM, MPa) of the hardened cements

| Cement | Thiourea derivative | FS [MPa] DS$^{a)}$ | FS [MPa] WS$^{b)}$ | FM [MPa] DS$^{a)}$ | FM [MPa] WS$^{b)}$ |
|---|---|---|---|---|---|
| Cat-1 + Base 1*) | Hexanoyl thiourea | 105.8 ± 2.0 | 97.8 ± 8.3 | 7121 ± 309 | 7790 ± 401 |
| Cat-1 + Base 2 | N-(2-Methacryloyloxyhexanoyl)thiourea (from Example 1) | 108.3 ± 6.4 | 111.1 ± 7.7 | 7113 ± 308 | 7793 ± 305 |
| Cat-1 + Base 3 | N-(4-Vinylbenzoyl)thiourea (from Example 2) | 91.4 ± 5.7 | 90.1 ± 7.6 | 7151 ± 193 | 7026 ± 443 |
| Cat-1 + Base 4*) | Allyl thiourea | 50.4 ± 7.9 | 50.8 ± 3.8 | 3256 ± 560 | 1929 ± 136 |
| Cat-1 + Base 5*) | Methacrylic acid 4-oxo-9-thioxo-5-oxa-3,8,10-triazatridec-12-en-1-yl ester (from Comparison Example 4) | 39.5 ± 2.5 | 34.7 ± 5.1 | 1676 ± 67 | 884 ± 81 |

*)Comparison example
$^{a)}$DS: Dry storage for 24 h at room temperature
$^{b)}$WS: Water storage for 24 h at 37° C.

The invention claimed is:

1. A radically polymerizable dental material, which comprises a combination of a thiourea derivative and a hydroperoxide as initiator system for the radical polymerization, characterized in that it comprises a thiourea derivative according to the following Formula (I):

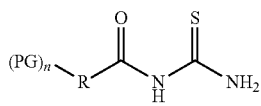

Formula I in which the variables have the following meanings:
R is absent or an (n+1)-valent, aromatic, aliphatic, linear or branched $C_1$-$C_{50}$ hydrocarbon radical, which can be interrupted by one or more, ether, thioether, ester, amide or urethane groups,
PG a radically polymerizable (meth)acrylate, (meth)acrylamide or vinyl group and
n is 1, 2 or 3.

2. The dental material according to claim 1, in which the variables have the following meanings:
R an (n+1)-valent, aromatic, aliphatic, linear or branched $C_1$-$C_{30}$ hydrocarbon radical, which can be interrupted by one or more ether, ester or urethane groups,
PG a radically polymerizable methacrylate, methacrylamide or vinyl group and
n is 1 or 2.

3. The dental material according to claim 2, in which the variables have the following meanings:
R an (n+1)-valent, aromatic, aliphatic, linear or branched $C_1$-$C_{20}$ hydrocarbon radical, which can be interrupted by 1 to 6 ether groups or one (1) ester or urethane group,
PG a radically polymerizable methacrylate or vinyl group,
n is 1
or
R a phenylene radical, a p-phenylene radical, or a radical with the formula -Ph-$CH_2$—,
PG a vinyl group and
n is 1.

4. The dental material according to claim 1, which comprises a compound of the formula $R^1$—$(OOH)_m$ as hydroperoxide, in which $R^1$ is an aliphatic or aromatic hydrocarbon radical and m is 1 or 2.

5. The dental material according to claim 4, which comprises t-amyl hydroperoxide, 1,1,3,3-tetramethylbutyl hydroperoxide, t-butyl hydroperoxide, t-hexyl hydroxyperoxide, 2,5-dimethyl-2,5-di(hydroperoxy)hexane, diisopropylbenzene monohydroperoxide, paramenthane hydroperoxide, p-isopropylcumene hydroperoxide or a mixture thereof, as hydroperoxide.

6. The dental material according to claim 1, which comprises a hydroperoxide according to the following Formula (II),

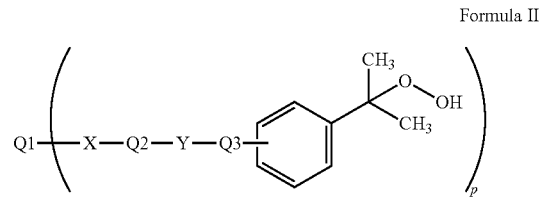

Formula II in which the variables have the following meanings:
$Q^1$ a p-valent, aromatic, aliphatic, linear or branched $C_1$-$C_{14}$ hydrocarbon radical, which can be interrupted by one or more S and/or O atoms and which can be unsubstituted or substituted by one or more substituents which are selected from —OH, —$OR^2$, —Cl and —Br, wherein $R^2$ is an aliphatic, linear or branched $C_1$-$C_{10}$ hydrocarbon radical,
X, Y independently of each other are in each case absent, —O—, —COO—; —$CONR^3$—, or —O—CO—$NR^4$—, wherein $R^3$ and $R^4$ independently of each other represent H or a $C_1$-$C_5$ alkyl radical,
$Q^2$ is absent, an aliphatic, linear or branched $C_1$-$C_{14}$ alkylene radical, which can be interrupted by S and/or O atoms and which can be unsubstituted or substituted by —OH, —$OR^5$, —Cl and/or —Br, wherein $R^5$ is an aliphatic, linear or branched $C_1$-$C_{10}$ hydrocarbon radical,
$Q^3$ a $C_1$-$C_3$ alkylene group or is absent,
wherein X and/or Y is absent if $Q^2$ is absent,
p 1, 2, 3 or 4, and wherein
the substitution on the aromatic compound takes place in position 2, 3 or 4.

7. The dental material according to claim 1, which additionally comprises a transition metal compound.

8. The dental material according to claim 1, which comprises
0.001 to 5 wt.-% at least one thiourea derivative of Formula (I),
0.01 to 5 wt.-% hydroperoxide,
optionally 0.0001 to 1 wt.-% transition metal compound,
in each case relative to the total mass of the material.

9. The dental material according to claim 1, which comprises
0.005 to 3.0 wt.-% at least one thiourea derivative of Formula (I),
0.05 to 4.0 wt.-% hydroperoxide,
optionally 0 0.0005 to 0.5 wt.-% transition metal compound,
in each case relative to the total mass of the material.

10. The dental material according to claim 1, which comprises
0.1 to 3.0 wt.-% at least one thiourea derivative of Formula (I),
0.1 to 3.0 wt.-% hydroperoxide,
optionally 0.0007 to 0.020 wt.-% transition metal compound,
in each case relative to the total mass of the material.

11. The dental material according to claim 1, which additionally comprises at least one radically polymerizable monomer, at least one mono- or multifunctional (meth)acrylate, at least one dimethacrylate or a mixture of mono- and dimethacrylates.

12. The dental material according to claim 11, which comprises methyl, ethyl, 2-hydroxyethyl, butyl, benzyl, tetrahydrofurfuryl or isobornyl (meth)acrylate, p-cumylphenoxyethylene glycol methacrylate (CMP-1E), 2-(2-bi-phenyloxy)ethyl methacrylate, bisphenol A dimethacrylate, an addition product of methacrylic acid and bisphenol A diglycidyl ether, ethoxylated or propoxylated bisphenol A dimethacrylate, 2-[4-(2-methacryloyloxyethoxyeth-oxy)phenyl]-2-[4-(2-methacryloyloxyethoxy)phenyl]propane) (SR-348c), 2,2-bis[4-(2-methacryloxypropoxy)phenyl]propane, an addition product of 2-hydroxyethyl methacrylate and 2,2,4-trimethylhexamethylene-1,6-diisocyanate, an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate, di-, tri- or tetraethylene glycol dimethacrylate, trimethylolpropane trimethacrylate, pentaerythritol tetramethacrylate, glycerol di- and trimethacrylate, 1,4-butanediol dimethacrylate, 1,10-decanediol dimethacrylate (D3MA), bis(meth-acryloyloxymethyl)tricyclo-[5.2.1.0$^{2,6}$]decane (DCP), a polyethylene glycol or polypropylene glycol dimethacrylate, polyethylene glycol 200 dimethacrylate, polyethylene glycol 400 dimethacrylate, 1,12-dodecanediol dimethacrylate or a mixture thereof, as radically polymerizable monomer.

13. The dental material according to claim 11, which additionally comprises at least one acid-group-containing radically polymerizable monomer, a polymerizable carboxylic acid, phosphonic acid, a polymerizable phosphoric acid ester or an anhydride of these substances.

14. The dental material according to claim 1, which additionally comprises at least one organic or inorganic filler, a nanoparticulate or microfine filler, a radiopaque filler, a ground prepolymer or a pearl polymer.

15. The dental material according to claim 1, which comprises
(a) 0.001 to 5.0 wt.-% of at least one thiourea derivative of Formula (I),
(b) 0.01 to 5.0 wt.-% of at least one hydroperoxide,
(c) 5 to 95 wt.-% filler(s), and
(e) 0.01 to 5 wt.-% additive(s),
in each case relative to the total mass of the material.

16. The dental material according to claim 1, which comprises
(a) 0.005 to 3.0 wt.-% of at least one thiourea derivative of Formula (I),
(b) 0.05 to 4.0 wt.-% of at least one hydroperoxide,
(c) 10 to 95 wt.-% of at least one radically polymerizable monomer,
(d) 0 to 80 wt.-% filler(s), and
(e) 0.1 to 3 wt.-% additive(s),
in each case relative to the total mass of the material.

17. The dental material according to claim 1, which comprises
(a) 0.1 to 3.0 wt.-% of at least one thiourea derivative of Formula (I),
(b) 0.1 to 3.0 wt.-% of at least one hydroperoxide,
(c) 10 to 90 wt.-% of at least one radically polymerizable monomer,
(d) 0 to 80 wt.-% filler(s), and
(e) 0.1 to 2 wt.-% additive(s),
in each case relative to the total mass of the material.

18. The dental material according to claim 16, which comprises 50 to 80 wt.-% filler when used as a filling composite, 10 to 70 wt.-% filler when used as a cement, and 0 to 10 wt.-% filler when used as a prosthesis material.

19. The dental material according to claim 1, for therapeutic use, as dental cement, filling composite or veneering material.

20. The dental material according to claim 1, for non-therapeutic use for the production or repair of dental restorations comprising prostheses, artificial teeth, inlays, onlays, crowns, bridges and complete dentures.

* * * * *